(12) United States Patent
Hashimoto

(10) Patent No.: US 6,251,075 B1
(45) Date of Patent: Jun. 26, 2001

(54) ULTRASONIC DIAGNOSIS APPARATUS

(75) Inventor: Keisuke Hashimoto, Nasu-gun (JP)

(73) Assignee: Kabushiki Kaisha Toshiba, Kawasaki (JP)

( * ) Notice: Subject to any disclaimer, the term of this patent is extended or adjusted under 35 U.S.C. 154(b) by 0 days.

(21) Appl. No.: 09/391,618

(22) Filed: Sep. 7, 1999

(30) Foreign Application Priority Data

Sep. 25, 1998 (JP) .................................................. 10-271298

(51) Int. Cl.$^7$ ........................................................ A61B 8/00
(52) U.S. Cl. .................................... 600/453; 600/453
(58) Field of Search .................................. 600/437, 443, 600/447; 73/625; 128/916; 367/138; 609/443, 449

(56) References Cited

U.S. PATENT DOCUMENTS

| 5,603,323 | * | 2/1997 | Pflugrath et al. | ..................... 600/443 |
| 5,795,297 | * | 8/1998 | Daigle | ................................. 600/447 |
| 6,102,864 | * | 8/2000 | Hatfiled et al. | ...................... 600/454 |
| 6,104,673 | * | 8/2000 | Cole et al. | ........................... 367/138 |

FOREIGN PATENT DOCUMENTS 6-343634 * 12/1994 (JP) .

* cited by examiner

Primary Examiner—Marvin M. Lateef
Assistant Examiner—Maulin Patel
(74) Attorney, Agent, or Firm—Oblon, Spivak, McClelland, Maier & Neustadt, P.C.

(57) ABSTRACT

An ultrasonic diagnosis apparatus has a plurality of units connected to each other via a particular data transmission path, the plurality of units including an ultrasonic probe, a transmission/reception control circuit, a blood flow analysis unit, a system storage, a display processing circuit, a display monitor and a CPU. Each of the units includes: data transfer means for transferring, to another unit, data having header information added thereto, the header information containing at least one of information concerning a data flow between the units on the data transmission path, and data processing information; and data processing means for processing data transferred from another unit with reference to the header information added to the data transferred from the another unit, and on the basis of the data processing information contained in the header information.

12 Claims, 3 Drawing Sheets

ULTRASONIC DIAGNOSIS APPARATUS

BACKGROUND OF THE INVENTION

This invention relates to an ultrasonic diagnosis apparatus for generating an ultrasonic image based on at least one of phase information and amplitude information contained in a signal that is created by scanning a cross section of a to-be-examined subject with an ultrasonic wave.

The conventional ultrasonic diagnosis apparatuses generally comprise a plurality of units corresponding to the manners of signal processing and image processing. These units are connected in the order according to the processes of the signal processing and image processing.

Interfaces of a fixed type corresponding to the order of connection of the units are each provided between a corresponding pair of adjacent units. A certain unit is arranged to process, in accordance with a predetermined timing signal, an image signal, for example, input thereto via a corresponding interface in a real-time manner, and then to output the process result to the next unit. Thus, in the conventional ultrasonic diagnosis apparatus, a series of processing is performed in a fixed order corresponding to the order of connection of the units.

FIG. 6 is a block diagram roughly illustrating the structure of the conventional ultrasonic diagnosis apparatus.

As is shown, the ultrasonic diagnosis apparatus comprises a plurality of units such as an ultrasonic probe 100, a rate pulse generating circuit 101, a transmission control circuit 102, a reception control circuit 103, a receiver 104, a digital scan converter (DSC) 105, an encoder 106, a monitor 107, a blood flow analysis unit 108 and a CPU unit 109.

When the operator has performed a predetermined operation for ultrasonic scanning, using, for example, an operation panel, the CPU unit 109 performs processing corresponding to the predetermined operation, thereby setting, in each unit, a parameter necessary for the ultrasonic scanning. In accordance with this setting, the rate pulse generating circuit 101 creates a basic signal (a rate pulse signal) for transmitting and receiving an ultrasonic wave. The transmission control circuit 102 drives the ultrasonic probe 100 to generate an ultrasonic pulse signal based on the basic signal. As a result, an ultrasonic pulse signal is transmitted from the ultrasonic probe 100 to a to-be-examined subject.

The ultrasonic probe 100 then receives a signal reflected from the subject. The reception control circuit 103 supplies the receiver 104 and the blood flow analysis unit 108 with the reflection signal received by the ultrasonic probe 100. As is shown in FIG. 7, the reception control circuit 103, which is called a "beam former", comprises pre-amplifiers 110 for amplifying a signal that indicates a received wave and is output from the ultrasonic probe 100, A/D converters (ADC) 111 for converting the amplified electric signals (analog signals) into digital signals, delay circuits 112 for delaying the digital signals from the respective ADCs 111, and an adder 113 for adding signals output from the delay circuits 112. The circuit 103 creates an ultrasonic reception signal, which is provided with predetermined directional characteristics by a received signal that has a predetermined delay corresponding to each ultrasonic oscillating element incorporated in the ultrasonic probe 100.

The receiver 104 subjects the received signal to predetermined signal processes such as quadrature detection, magnitude detection, filter processing, edge emphasis processing, etc., and outputs the process result, e.g. a B-mode image signal, to the DSC 105 provided after the receiver 104.

The blood flow analysis unit 108 performs signal processing such as MTI filtering, autocorrelation processing, etc., thereby generating a two-dimensional blood flow signal indicative of flow velocity, power, dispersion, etc. An FFT unit incorporated in the blood flow analysis unit 108 calculates a flow velocity distribution. The signal processing results of the blood flow analysis unit 108 are supplied to the DSC 105, superposed therein upon the B-mode image signal output from the receiver 104, and developed into a two-dimensional image. The two-dimensional image is converted by the encoder 106 into a video signal that can be displayed on, for example, a TV monitor, and is then displayed on the monitor 107.

The above-described conventional ultrasonic diagnosis apparatus has the following problems:

(1) A series of ultrasonic scanning, signal processing and display processing are performed in a fixed order as aforementioned, and therefore it is difficult to add a new function so as to enhance the performance of the apparatus.

(2) The unit structure is hard to change since it is limited by the interface rules. This means that to reduce the size or cost of the apparatus is difficult.

(3) The data flow between units is also hard to change, and hence it is difficult to access data from each unit in a desired manner. Data indicating a signal or an image obtained by ultrasonic scanning is dispersed and stored, while it is processed, in storage devices that are incorporated in the units. To access desired data from a unit for special processing other than usual image display processing, it is necessary to provide an exclusive signal line used for reading data from, for example, the CPU, as well as a signal line for usual image display. Also from the viewpoint of cost reduction of the apparatus, it is not preferable to disperse signals or images into storage devices of the units.

(4) When, for example, a failure has occurred in a particular unit, the function of the unit (for example, the blood flow display function of the blood flow analysis unit) cannot be provided unless the unit is exchanged for a new one.

BRIEF SUMMARY OF THE INVENTION

The present invention has been developed under the above-described circumstances, and is aimed at providing an ultrasonic diagnosis apparatus capable of realizing a data flow of high freedom between a plurality of units connected to each other via a general-purpose data transmission path.

According to the present invention, there is provided an ultrasonic diagnosis apparatus comprising: an ultrasonic probe for emitting an ultrasonic wave to a subject to be examined, receiving a wave reflected from the subject, and outputting a signal corresponding to the reflected wave; a beam former unit for generating RF data based on the signal corresponding to the reflected wave and output from the ultrasonic probe; a receiver unit for generating detection data based on the RF data; a scan converter unit for generating image data based on the detection data; a bus connected to the beam former unit, the receiver unit and the scan converter unit for transferring the RF data, the detection data and the image data between the units; and control means for controlling a data flow between the units.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE INVENTION

The embodiments of the invention will be described with reference to the accompanying drawings.
(First Embodiment)

Figure 1:
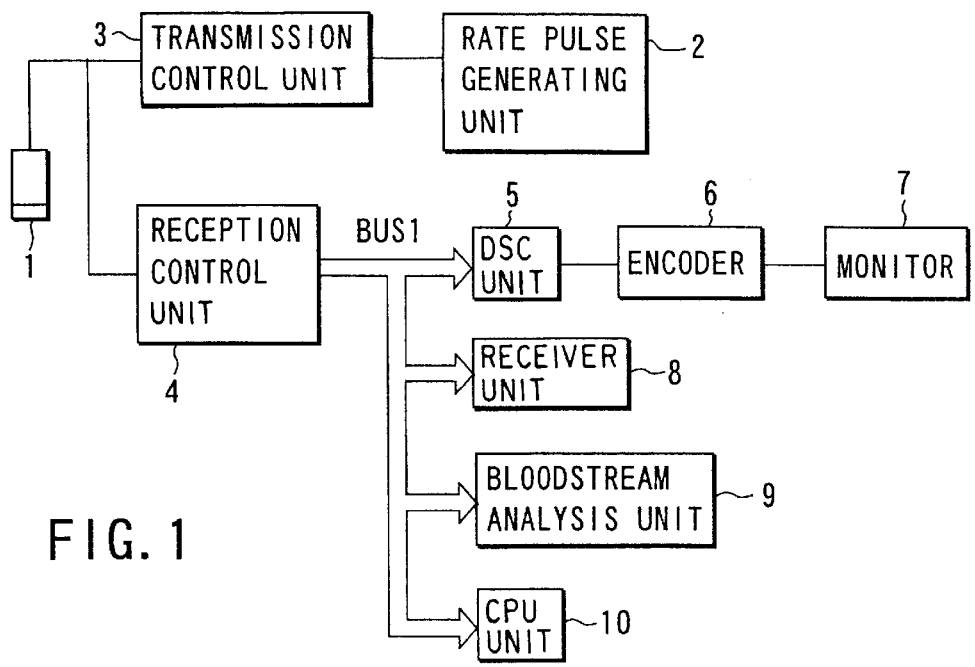
FIG. 1 is a schematic block diagram illustrating an ultrasonic diagnosis apparatus according to a first embodiment of the invention.

FIG. 1 is a schematic block diagram illustrating an ultrasonic diagnosis apparatus according to a first embodiment of the invention. As shown, the ultrasonic diagnosis apparatus of this embodiment comprises a plurality of units such as an ultrasonic probe 1, a rate pulse generating unit 2, a transmission control unit 3, a reception control unit 4, a DSC (Digital Scanner Converter) unit 5, an encoder 6, a monitor 7, a receiver unit 8, a blood flow analysis unit 9 and a CPU unit 10. Each unit has the same basic function as that of the conventional apparatus.

The ultrasonic probe 1 emits an ultrasonic wave to a to-be-examined subject, receives a wave reflected therefrom and outputs an electric signal corresponding to the reflected wave.

The reception control unit 4 serves as a beam former unit for creating RF data based on the electric signal that corresponds to the reflection wave received by the ultrasonic probe 1, and comprises pre-amplifiers, A/D converters and delay circuits, which correspond to the channels of respective ultrasonic oscillator elements. The unit 4 also includes an adder for adding signals output from the delay circuits. The RF data is a signal modulated using an ultrasonic transmission frequency, or a signal obtained after quadrature detection is performed using the ultrasonic receiving reference frequency. The RF data has a bit width of 16–18 bits. The band width of the RF data depends upon a used ultrasonic probe or ultrasonic transmission frequency, but is usually about 2–10 MHz.

The receiver unit 8 is a unit for performing magnitude detection on the RF data output from the reception control unit 4, thereby generating a signal for a tissue form information image (a B-mode image). The receiver unit 8 includes an magnitude detection circuit for performing magnitude detection. In the magnitude detection processing, an RF signal output from the beam former is subjected to magnitude detection, and data of 8–12 bits obtained by subjecting the resultant signal to logarithm compression processing is output.

The blood flow analysis unit 9 comprises an quadrature detection circuit, an FFT circuit and a CFM circuit. The quadrature detection circuit includes a mixer, a phase shifter, a low-pass filter, etc., and performs quadrature detection processing on the RF data to thereby output an I (In phase) signal of 16 bits and a Q (Quadrature phase) signal of 16 bits as detection signals expressed in a complex form.

The FFT circuit creates FFT data by subjecting the I signal and the Q signal to frequency analysis processing (FFT). The FFT data is a signal indicating the power and direction of a blood flow signal, and has a bit width of 16 bits. In accordance with predetermined FFT conditions, 32–512 samples that define the frequency resolution are used.

The CFM circuit creates CFM data indicating the velocity, power or dispersion of a moving object such as a blood flow, by applying the autocorrelation operation method to the I and Q signals. The power data is mainly grouped into one obtained by an operation performed simultaneous with velocity and dispersion operations, and one obtained by an operation using the power Doppler method. The power Doppler method usually cannot detect the direction of the blood flow. However, there is also known a power Doppler method which enables recognition of the blood flow direction using a sign obtained by the autocorrelation operation.

The bit width of color data usually is set at 8 bits, while that of power data may be set at 16 bits. One bit as a sign bit is usually assigned to data indicating, for example, the velocity.

The DSC unit 5 is a scan converter unit for creating image data. The image data is obtained by subjecting the detection data, the FFT data or the CFM data to image conversion processing performed by the scan converter. These data items are usually converted into image data of 512×512 pixels. The data width is 8–12 bits.

The above-described beam former unit, the receiver unit, the blood flow analysis unit and the scan converter unit are connected to the bus 1, thereby transferring the RF data, the Doppler data and the image data between the units. The data flow between the units is controlled by the CPU unit 10.

The bus 1 as a data transmission path is a general-purpose bus such as a bus based on the PCI (Peripheral Component Interconnect) standard, which does not depend upon a particular system (CPU). It is a matter of course that the invention is not limited to the PCI bus.

Data obtained by ultrasonic scanning is transferred between the units always via the bus 1. To avoid simultaneous occurrence of different types of data transfer and hence occurrence of conflict therebetween, an arbiter circuit (not shown) is provided in the bus 1. Further, the bus 1 has a high data transfer rate which enables desired data transfer, and has a wider bus width than the data width. Alternatively, the bus 1 operates in accordance with a clock signal of a higher rate than a data collection rate.

A specific connection between the bus 1 and the local bus will be described.

Figure 2:
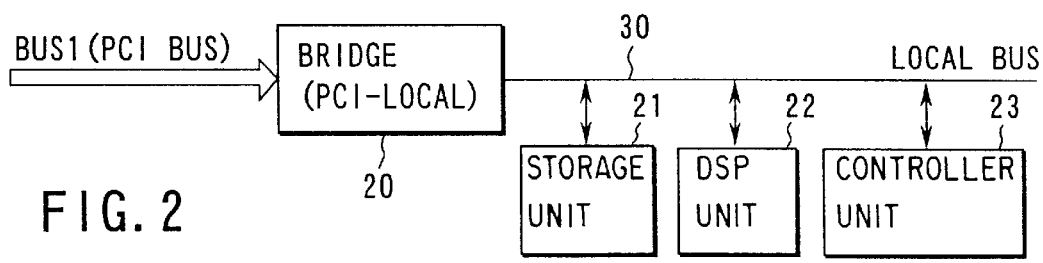
FIG. 2 is a block diagram illustrating a connection between a bus 1 and a local bus.

FIG. 2 is a block diagram showing a connection between the bus 1 and the local bus. As shown, the bus 1 is connected to a local bus 30 via a bridge 20. The local bus 30 is connected to a DSP (Digital Signal Processor) unit 22 as a signal processing unit, a storage unit 21 for temporarily storing to-be-processed data, and a controller unit 23 for arbitrating the access right of the local bus 30. The bridge 20 performs the protocol conversion of the bus 1 (PCI bus) and the local bus 30.

Each unit connected to the bus 1 has data transfer means for transferring, to another unit, data with header information that includes information on a data flow and information on data processing performed between the units on the bus 1.

The data flow information indicates the flow of data between the units on the bus 1. More specifically, it indicates address information or buffer size information which is used when a certain unit (e.g. the CPU) instructs another predetermined unit to perform processing and sends the processing result to yet another unit. The buffer size information indicates the sizes of to-be-transferred control data and actual data. The data flow information can have any desired format (data structure), but it is desirable that the units connected by the bus 1 should have a single format.

The data processing information indicates how each unit should process data. The data processing information can have any desired format, too, but it is also desirable that the units connected by the bus 1 should have a single format.

Each unit has, as well as the data transfer means, data processing means for processing data transferred from another unit, referring to the data processing information contained in the header information added to the to-be-processed data.

The operation of the ultrasonic diagnosis apparatus of the first embodiment constructed as above will be described.

First, initial setting for data transfer control on the bus 1 is executed. This initial setting is performed when turning on or resetting the ultrasonic diagnosis apparatus of the embodiment. At the initial setting, the CPU unit 10 sets, for each unit connected to the bus 1, address information that indicates a destination to which data is to be transferred, and buffer size information. Thus, an optional address on the bus 1 is assigned to each unit, which means that each unit has a corresponding destination address.

Under the control of the CPU unit 10, the rate pulse generating unit 2 generates a basic signal (rate pulse signal) for ultrasonic transmission and reception. The transmission control unit 3 drives the ultrasonic probe 1 to generate an ultrasonic pulse signal based on the basic signal. As a result, the ultrasonic probe 1 emits an ultrasonic pulse signal to the to-be-examined subject.

Then, the ultrasonic probe 1 receives a wave reflected from the subject. At this time, the reception control unit 4 creates RF data based on an electric signal that indicates the reflected wave received by the ultrasonic probe 1, and transfers the RF data to the receiver unit 8 via the bus 1. In other words, the reception control unit 4 designates an address contained in the data flow information and assigned to the receiver unit 8, and supplies the receiver unit 8 with the RF data having the address-designated header information added. Thus, the receiver unit 8 acquires RF data necessary for B-mode display. Also, the reception control unit 4 designates an address contained in the data flow information and assigned to the blood flow analysis unit 9, and supplies the unit 9 with the RF data having the address-designated header information added. Thus, the blood flow analysis unit 9 acquires RF data necessary for blood flow analysis.

The receiver unit 8 subjects the supplied RF data to predetermined signal processing necessary for B-mode display, such as magnitude detection processing, filtering, edge emphasis processing, etc., thereby obtaining detection data and transferring it to the DSC unit 5 via the bus 1.

On the other hand, the blood flow analysis unit 9 creates CFM data concerning flow velocity, power, dispersion, etc. for creating a two-dimensional blood flow signal, by signal processing such as MTI filtering, autocorrelation processing, etc. Further, the FFT unit calculates a distribution of flow velocity. The CFM data and the FFT data are transferred to the DSC unit 5 via the bus 1, superposed upon a B-mode image signal transferred from the receiver unit 8, and developed into a two-dimensional image. The two-dimensional image is converted by the encoder 6 into a signal based on the SVGA or NTSC standard which enables display of the signal on, for example, a TV monitor, and is then displayed on the monitor 7. A digital signal interface such as an LCD may be provided.

The above-described ultrasonic diagnosis apparatus can realize the following functions:

(1) Image Storage Function Using System Storage Various functions as described blow can be realized by transferring, via the bus 1 to a system storage (not shown) managed by the CPU unit 10, data collected at the time of ultrasonic scanning, such as an output signal from the receiver unit 8, or image data indicating an ultrasonic image and created by the DSC unit 5 on the basis of the collected data.

[Reprocessing]

Reprocessing can be realized by reading particular data from a system storage that stores ultrasonic data or image data, then transferring it to a unit, and again performing image processing with the transferred data provided with a parameter different from that imparted in the last occasion. It is a matter of course that re-processing (simple reproduction) may be performed by supplying the data with the same parameter as in the last occasion.

More specifically, the power Doppler mode operation can be performed to display an image of blood flow while fetching RF data for a color data operation by the CPU unit 10. For example, a blood flow image using a different parameter can be displayed by performing re-operation in the velocity/dispersion mode but not in the power Doppler mode, after freezing the display. Application of the FFT method can be considered as a color operation.

[Common Use Of Operation Processing Unit]

Common processing can be executed by a single operation processing unit or the CPU connected to the bus.

For example, the following processes (A) and (B) can be executed by a single operation processing unit or the CPU.

(A) Flash Echo Imaging

An ultrasonic contrast medium is broken by a high power ultrasonic pulse signal within a living body. In the Flash Echo Imaging method, the difference between an image signal obtained by ultrasonic scanning using a low power ultrasonic pulse signal, and an image signal obtained by ultrasonic scanning using a high intensity ultrasonic pulse signal is calculated, thereby imaging only a portion in which the ultrasonic contrast medium is accumulated.

More specifically, ultrasonic images obtained before and after the bubble destruction of a contrast media and stored in the storage of the DSC unit 5 are read therefrom via the bus 1, thereby executing subtraction processing between the images and supplying the subtraction result to the DSC unit 5.

(B) Calculation Of Acceleration Parameter In Color Doppler Method

The difference between present velocity data and velocity data one frame before, obtained by the color operation, is calculated to thereby calculate an acceleration parameter.

More specifically, differential processing is performed on CFM (Color Flow Mapping) data items obtained at different points in time and sent from the blood flow analysis unit 9 via the bus 1, thereby obtaining an acceleration parameter and supplying it to the DSC unit 5.

[Substitution Of Blood flow Analysis Unit By CPU]

If during the ultrasonic scanning, obtained data is transferred to the system storage, the CPU unit 10, in place of the blood flow analysis unit 9, can perform the CFM (Color Flow Mapping) operation and the FFT operation (frequency analyzing operation) with reference to the transferred data, and transfer the operation results to the next unit (e.g. the DSC unit 5) via the bus 1. Thus, blood flow data can be displayed, using the CPU unit 10 instead of the blood flow analysis unit 9.

The following processing can also be executed. Blood flow data is not displayed during the ultrasonic scanning (or is displayed at a low frame rate), and the CPU unit 10 performs the CFM operation with reference to data in the system storage for the first time when the operator has instructed, for example, to freeze the display, thereby displaying blood flow data at a high frame rate. As a result, the load on the CPU unit 10 can be appropriately dispersed, and hence the apparatus can operate in a stable manner. The FFT operation can also be performed in a similar manner to the above.

It is not only the blood flow analysis unit 9 that can be substituted by the CPU unit 10. For example, the DSC unit 5 may be substituted by the CPU unit 10. In this case, the CPU unit 10 refers to data transferred to the system storage, and performs operations for display processing.

[Decimation (Reduction of data amount)]

When executing the above-described image storage function, it is preferable to reduce the load on the bus 1 by using decimation technique so that the amount of data in one line of the ultrasonic raster deduce to a predetermined constant amount or less within a range in which a predetermined image quality can be obtained.

(2) Function For Facilitating Construction of Hardware Structure

[Addition Or Upgrading Of Unit]

Addition or upgrading of a unit in accordance with the addition of a system function can be realized easily since the interfaces are based on the same standard.

It is effective to pick out RF data, output from the reception control unit 4 (the beam former unit), via the bus 1 before it is processed by the receiver unit 8 (the detection unit), and to process it by an additional operation unit.

[Parametric Imaging]

The following processing can be executed:

A predetermined ROI (Region Of Interest) is set for the RF data by an operation unit (the CPU unit 10 can be used in place of this unit) additionally connected to the bus 1, thereby calculating the integrated backscatter of a signal band included in the ROI. The ROI is shifted, and the integrated backscatter values of predetermined depths of a beam are obtained, transferred to the DSC unit 5, and converted into an image. If filtering is necessary to reduce the noise, the obtained integrated backscatter values are transferred to the receiver unit 8, and filtered therein. Since in this case, the magnitude detection, the logarithm compression operation, etc. are not necessary, it is necessary to set the header information so that these processes will not be performed. The integrated backscatter values filtered by the receiver unit 8 are transferred to the DSC unit 5 and converted into an image therein.

[Elasticity Imaging]

An elasticity parameter image can also be obtained by calculating the elasticity (elasticity parameter) of a tissue by interpolation calculation of data acquired before and after pressing the tissue, then transferring the calculation result to the DSC unit 5 and imaging it therein. If filtering is necessary to reduce the noise, the same processing as above is performed.

This processing is executed on the basis of the RF data. After elasticity imaging by the CPU unit 10, the imaging result is supplied to the DSC unit 5.

[Frequency-Dependent-Attenuation Imaging]

In a living tissue, an attenuation in the intensity of an ultrasonic signal increases as the frequency of the signal increases. Further, the attenuation increases when a soft tissue suffers from a disease and hardens. If, for example, the zero-crossing method is used to calculate, for each of predetermined depths, the number of occasions in which the RF data crosses zero, a two-dimensional image can be obtained by the estimation of the average frequency of the ultrasonic signal. The obtained image visually indicates the attenuation depending upon the frequency. A method for calculating the inclination of a spectrum by the FFT can be employed as well as the zero-crossing method.

This processing is executed on the basis of the RF data. After frequency-dependent-attenuation imaging by the CPU unit 10, the imaging result is supplied to the DSC unit 5.

[Reduction Of Near Field Fixed Noise]

When imaging, for example, the heart using an ultrasonic probe of a sector electronic scan type, it is possible that multipath reflection will occur at a costa or at the probe housing and hence fixed noise will occur in the near filed of the image of the probe. Since this noise is similar to the DC component, it can be reduced by subjecting the RF data to high-pass filtering in a frame direction. After this noise removal processing is performed as a pre-process, usual imaging processing is executed. As a result, a high quality image is provided. It should be noted that the noise removal processing is not necessary for the imaging of an abdominal section.

This processing is executed on the basis of the RF data. After low-pass filtering processing by the CPU unit 10, the processing result is supplied to the receiver unit 8. The receiver unit 8, in turn, executes magnitude detection processing on the low-pass filtered signal, and supplies the resultant signal to the DSC unit 5.

As aforementioned, the connection order of units in the conventional diagnosis apparatus is fixed. In the ultrasonic diagnosis apparatus of the invention, however, a plurality of units are connected to the bus 1, and data transfer is executed between the units on the basis of data flow information. Therefore, the connection order of the units is optional and the order of processes performed by the units can easily be changed.

[At Failure]

The hardware structure (the connection structure of the units) can be dynamically changed in accordance with the results of failure diagnosing processing performed when the apparatus is turned on, or by an instruction from the user. If, for example, the conventional ultrasonic diagnosis apparatus has a unit that is out of order, it cannot be used. On the other hand, in the apparatus of the present invention, the hardware can be dynamically changed by separating any troubled unit from the bus 1. Accordingly, the inoperable state of the entire apparatus can be avoided although its function is partially limited. Moreover, the troubled unit may be substituted by another unit (for example, the CPU unit 10). In this case, it suffices if the address of the troubled unit as a data transfer destination is dynamically changed.

As described above, the first embodiment can realize a data flow of high freedom between a plurality of units connected to each other via the general-purpose PCI bus.

(Second Embodiment)

A second embodiment of the invention will now be described.

In the above-described ultrasonic diagnosis apparatus of the first embodiment, a single bus is connected to the units. On the other hand, an ultrasonic diagnosis apparatus according to the second embodiment employs two buses connected to the units, which is the feature of the second embodiment.

Figure 3:
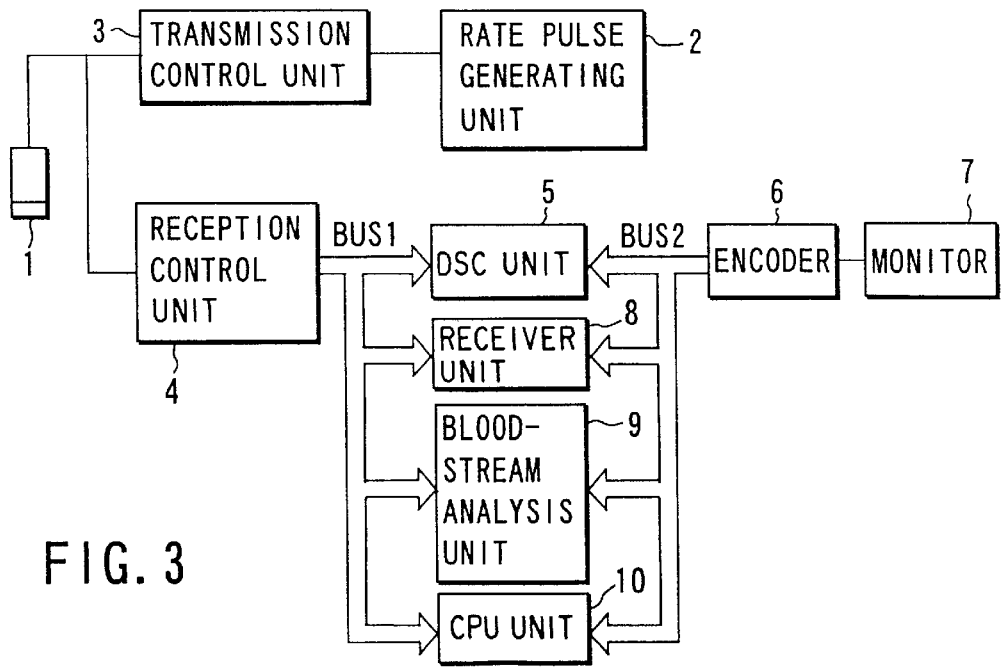
FIG. 3 is a schematic block diagram showing an ultrasonic diagnosis apparatus according to a second embodiment of the invention.

FIG. 3 is a block diagram schematically illustrating the ultrasonic diagnosis apparatus of the second embodiment. This apparatus comprises the same units as the apparatus of the first embodiment. However, in the apparatus of the second embodiment, the reception control unit 4 is connected to the bus 1, whereas the DSC unit 5, the receiver unit 8, the blood flow analysis unit 9 and the CPU unit 10 are connected to both the bus 1 and a bus 2, as is shown in FIG. 3.

The buses 1 and 2 as data transfer lines may be based on the same bus standard or on different bus standards.

In the apparatus of the second embodiment, a data flow which enables dynamic dispersion of bus load can be realized between the buses 1 and 2. Alternatively, this apparatus may have a bus structure in which the use of the buses 1 and 2 is limited. In this case, for example, the bus 1 is used for various data transfer between the units, and the bus 2 is exclusively used for data transfer from the DSC unit 5 to the encoder 6.

The data flow which enables dynamic dispersion of bus load between the buses 1 and 2 is, for example, as follows.

When performing ultrasonic scanning where only B-mode display is executed, the blood flow analysis unit 9 is in the idling state. The CPU unit 10 causes the output of the reception control unit 4 to be transferred to the receiver unit 8 via the bus 1, and causes the output of the receiver unit 8 to be transferred to the DSC unit 5 via the bus 1. The output of the DSC unit 5 is transferred to the encoder 6 via the bus 2.

Since in the B-mode display, the frame rate of ultrasonic image display is high, a large amount of data is transferred from the DSC unit 5 to the encoder 6. Therefore, part of the load on the bus 2 is shifted to the bus 1.

On the other hand, when performing blood flow analysis display (color scanning), the frame rate is low, and the blood flow analysis unit 9 performs data transfer at a high frequency. To shift part of the load on the bus 1 to the bus 2, the bus 1 is used to transfer the output of the receiver unit 8 to the blood flow analysis unit 9, while the bus 2 is used to transfer the output of the receiver unit 8 to the DSC unit 5. Since the blood flow analysis unit 9, which obtains blood flow data by scanning the same position of a subject several times, outputs a smaller amount of data than its input data, the bus 1 may be used for data transfer from the blood flow analysis unit 9 to the DSC unit 5. The output of the DSC unit 5 is transferred to the encoder 6 via the bus 2.

A description will be given of an embodiment concerning a specific connection between the buses 1 and 2 and a local bus 30.

Figure 4:
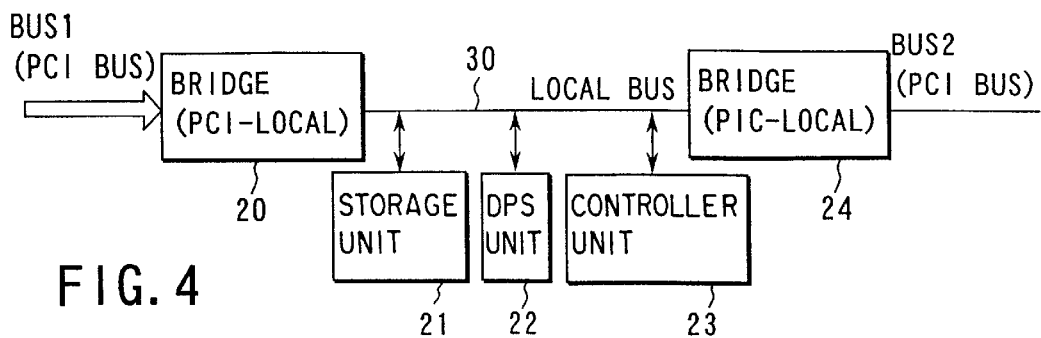
FIG. 4 is a block diagram illustrating a connection between a bus 1, a bus 2 and a local bus.

FIG. 4 is a block diagram illustrating a connection between the buses 1 and 2 shown in FIG. 3 and the local bus 30. As is shown in FIG. 4, the bus 1 is connected to the local bus 30 via a bridge 20, and the bus 2 is connected to the local bus 30 via a bridge 24.

The local bus 30 is connected to a DSP (Digital Signal Processor) unit 22 as a signal processing unit, a storage unit 21 for temporarily storing processing data, and to a controller unit 23 for arbitrating the access right of the local bus 30. The bridge 20 performs protocol conversion between the bus 1 (a PIC bus in the FIG. 4 case) and the local bus 30.

Figure 5:
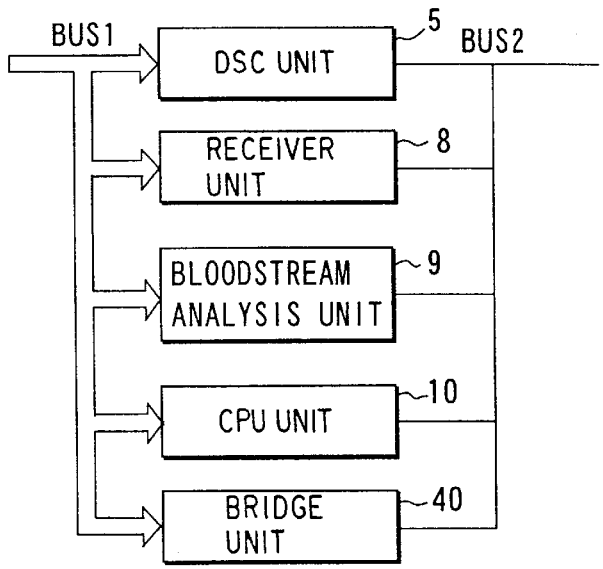
FIG. 5 is a schematic block diagram showing a modification of the ultrasonic diagnosis apparatus according to the second embodiment of the invention.
Figure 6:
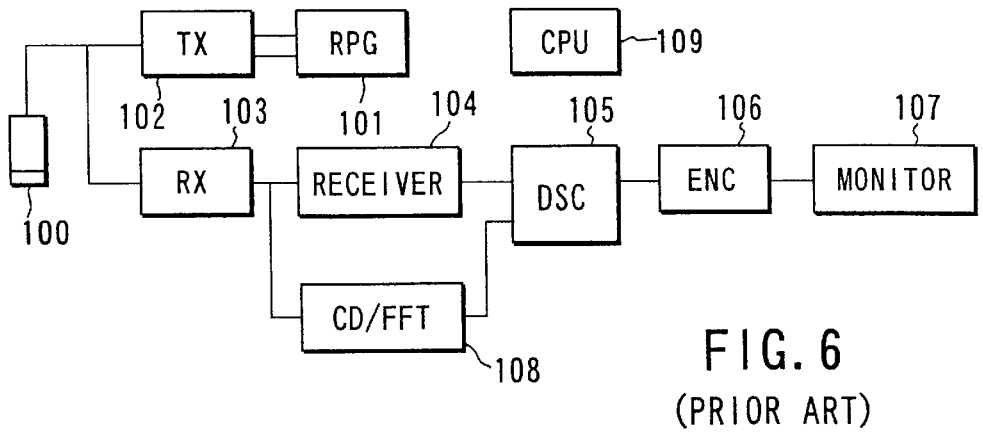
FIG. 6 is a schematic block diagram showing the conventional ultrasonic diagnosis apparatus.
Figure 7:
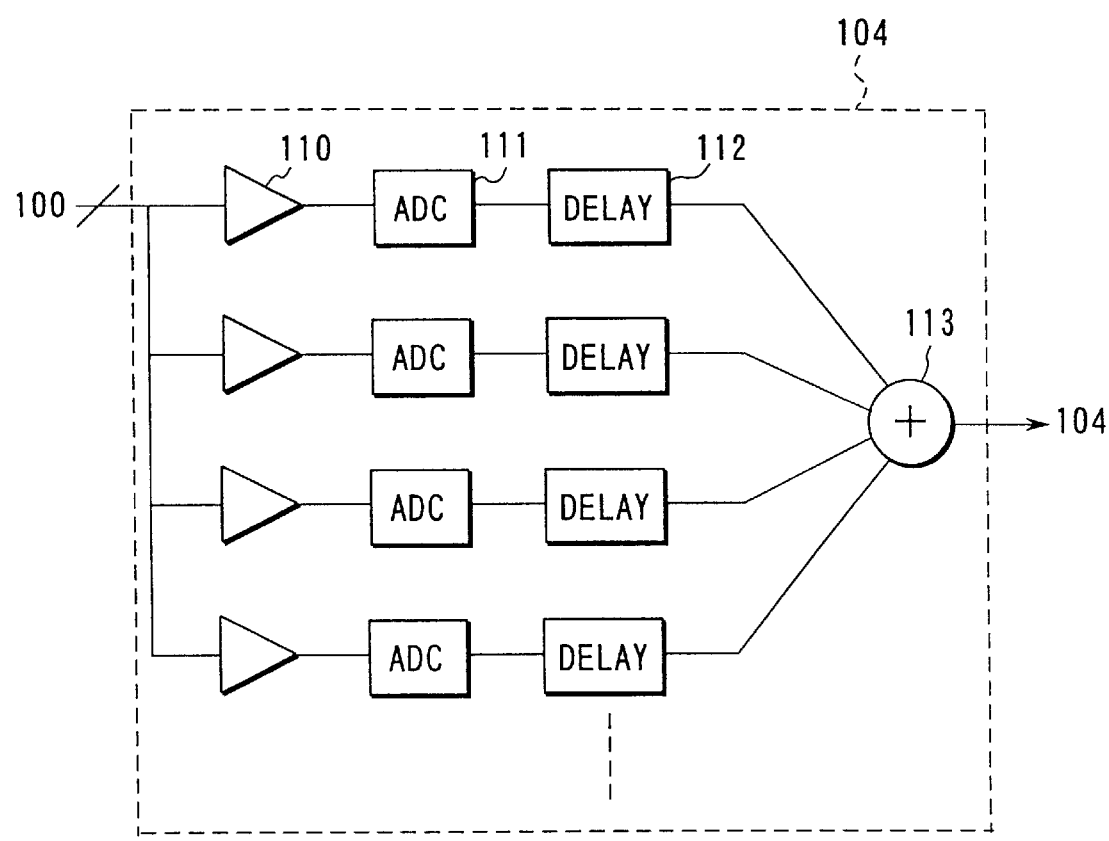
FIG. 7 is a schematic block diagram illustrating a reception control circuit incorporated in the conventional ultrasonic diagnosis apparatus.

FIG. 5 is a block diagram schematically illustrating an ultrasonic diagnosis apparatus according to a modification of the second embodiment.

As is shown in FIG. 5, a single logical bus may be constructed by connecting the buses 1 and 2 to each other via a bridge unit 40. In this case, each of the buses 1 and 2 as physical buses can perform data transfer independent of each other.

The above-described ultrasonic diagnosis apparatus of the second embodiment can realize a function equivalent to that of the first embodiment, and also can stabilize data transfer on the buses by appropriately dispersing the bus load.

The invention is not limited to the above-described embodiments but can be modified in various manners. For example, the aforementioned unit structure is just an example. The ultrasonic diagnosis apparatus of the invention can have a different unit structure in which a unit other than the aforementioned ones may be added or none of the aforementioned units may be employed.

Although in the above-described embodiments, RF data is supplied from the reception control unit 4 to the other units, this structure may be modified such that an quadrature detection circuit is provided in the reception control unit 4, and the I and Q signals are supplied from the unit 4 to the other units. In this case, the receiver unit 8 obtains an magnitude detection signal from the I and Q signals, and outputs a resultant signal to the DSC unit 5. The FFT and CFM circuits of the unit 9, in turn, execute processing based on the I and Q signals. This structure enables simplification of the detection processing by the receiver unit 8, and makes the detection circuit unnecessary in the blood flow analysis unit 9. As a result, the entire apparatus can be simplified in structure. Furthermore, I and Q signals which contain less data than the RF data can be obtained by performing decimation processing which reduce the amount of I and Q signal data in the reception control unit 4. In this case, the amount of to-be-transferred data and accordingly the load on the bus 1 reduce.

As described above, the invention can provide an ultrasonic diagnosis apparatus capable of realizing a data flow of high freedom between a plurality of units connected to each other via a general-purpose data transmission path. This ultrasonic diagnosis apparatus can be manufactured to a small size at a low cost, and has an excellent extensibility.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasonic diagnosis apparatus comprising:
   an ultrasonic probe configured to emit an ultrasonic wave to a subject to be examined, receive a wave reflected from the subject, and output a signal corresponding to the reflected wave;
   a beam former unit configured to generate RF data obtained by a delay and adding method from an output signal of the ultrasonic probe;
   a receiver unit configured to generate detection data based on the RF data;
   a scan converter unit configured to generate image data based on the detection data;
   a bus connected to the beam former unit, the receiver unit and the scan converter unit and configured to transfer the RF data and the detection data between the units; and
   a controller configured to control a data flow between the units.

2. An apparatus according to claim 1, further comprising a Doppler unit connected to the bus and configured to generate, from the RF data, two-dimensional Doppler data corresponding to a moving object and based on an ultrasonic color Doppler method.

3. An ultrasonic diagnosis apparatus having a plurality of units connected to each other via a bus, the plurality of units including a transmission/reception control unit, a blood flow analysis unit, a display processing unit, and a B-Mode processing unit,
   wherein each of the units includes:
   a transfer controller configured to transfer, to another unit, data having header information added thereto, the header information containing at least one of information concerning a data flow between the units, and data processing information; and
   a data processor configured to process data transferred from another unit with reference to the header information added to the data transferred from said another unit, and on the basis of the data processing information contained in the header information.

4. An apparatus according to claim 3, wherein the bus is connected to a local bus via a bridge device.

5. An ultrasonic diagnosis apparatus comprising:

an ultrasonic probe having a plurality of ultrasonic oscillation elements configured to emit an ultrasonic wave to a subject to be examined, receive a wave reflected from the subject, and output a signal corresponding to the reflected wave;

a delay adder device configured to subject the signal output from the ultrasonic probe, to delay adding processing;

a quadrature detection device configured to subject data obtained by the delay adding processing, to quadrature detection, and output a quadrature detection data expressed in a complex form;

a bus for signal transmission;

a B-Mode processing device configured to generate B-Mode data based on the quadrature detection data supplied via the bus;

a CFM processing device configured to generate CFM data based on the quadrature detection data supplied via the bus; and an image processing device configured to generate display image data based on the B-Mode data and the CFM data supplied via the bus.

6. An ultrasonic diagnosis apparatus comprising:

an ultrasonic probe having a plurality of ultrasonic oscillation elements configured to emit an ultrasonic wave to a subject to be examined, receive a wave reflected from the subject, and output a signal corresponding to the reflected wave;

a reception control device having a delay adder configured to subject the signal output from the ultrasonic probe, to delay adding processing;

a bus for signal transmission;

a B-Mode processing device configured to generate B-Mode data based on an output of the reception control device supplied via the bus;

a CFM processing device configured to generate CFM data based on the output of the reception control device supplied via the bus; and an operation processing device configured to perform various operations on the basis of data sent via the bus, the operation processing device generating CFM data based on the output of the reception control device when the CFM processing device is out of order.

7. An apparatus according to claim 6, wherein the operational device executes at least one of flash echo processing, arithmetic processing for obtaining an acceleration parameter used in a color Doppler method, parameter image processing, elasticity imaging processing, short-distance fixed noise removal processing and frequency-dependent-attenuation imaging processing.

8. An ultrasonic diagnosis apparatus comprising:

an ultrasonic probe having a plurality of ultrasonic oscillation elements configured to emit an ultrasonic wave to a subject to be examined, receive a wave reflected from the subject, and output a signal corresponding to the reflected wave;

a reception control device having a delay adder configured to subject the signal output from the ultrasonic probe, to delay adding processing;

a bus for signal transmission;

a B-Mode processing device configured to generate B-Mode data based on an output of the reception control device supplied via the bus;

a CFM processing device configured to generate CFM data based on the output of the reception control device supplied via the bus; and an operation processing device configured to perform various operations on the basis of data sent via the bus, the operation processing device generating the B-Mode data based on the output of the reception control device when the B-Mode processing device is out of order.

9. An apparatus according to claim 8, wherein the operational device executes at least one of flash echo processing, arithmetic processing for obtaining an acceleration parameter used in a color Doppler method, parameter image processing, elasticity imaging processing, short-distance fixed noise removal processing and frequency-dependent-attenuation imaging processing.

10. An ultrasonic diagnosis apparatus comprising:

an ultrasonic probe having a plurality of ultrasonic oscillation elements configured to emit an ultrasonic wave to a subject to be examined, receive a wave reflected from the subject, and output a signal corresponding to the reflected wave;

a reception control device having a delay adder configured to subject the signal output from the ultrasonic probe, to delay adding processing;

a bus for signal transmission;

a B-Mode processing device configured to generate B-Mode data based on an output of the reception control device supplied via the bus;

a CFM processing device configured to generate CFM data based on the output of the reception control device supplied via the bus; and an image processing device configured to generate display image data based on the B-Mode data and the CFM data sent via the bus.

11. An apparatus according to claim 10, wherein the B-Mode processing device and the CFM processing device process an quadrature detection signal sent from the reception control device and expressed in a complex form.

12. An ultrasonic diagnosis apparatus comprising:

an ultrasonic probe having a plurality of ultrasonic oscillation elements configured to emit an ultrasonic wave to a subject to be examined, receive a wave reflected from the subject, and output a signal corresponding to the reflected wave;

a delay adder device configured to subject a signal output from the ultrasonic probe, to delay adding processing;

a bus for signal transmission;

a B-Mode processing device configured to generate B-Mode data based on the output of the delay adder device supplied via the bus;

a CFM processing device configured to generate CFM data based on the output of the delay adder device supplied via the bus; and an image processing device configured to generate display image data based on the B-Mode data and the CFM data supplied via the bus.

* * * * *